United States Patent
Fueyo et al.

(10) Patent No.: US 8,126,228 B2
(45) Date of Patent: *Feb. 28, 2012

(54) DETERMINING EFFICACY OF THERAPEUTIC INTERVENTION IN NEUROSYCHIATRIC DISEASE

(75) Inventors: Joanna Lynn Fueyo, Brighton, MA (US); Robert Lee Angell, Salt Lake City, UT (US); Robert R. Friedlander, Southbury, CT (US); James R. Kraemer, Santa Fe, NM (US)

(73) Assignee: International Business Machines Corporation, Armonk, NY (US)

( * ) Notice: Subject to any disclaimer, the term of this patent is extended or adjusted under 35 U.S.C. 154(b) by 924 days.

This patent is subject to a terminal disclaimer.

(21) Appl. No.: 12/141,322

(22) Filed: Jun. 18, 2008

(65) Prior Publication Data

US 2009/0316969 A1     Dec. 24, 2009

(51) Int. Cl.
*G06K 9/00* (2006.01)
(52) U.S. Cl. ........................................................ 382/128
(58) Field of Classification Search .................. 382/128
See application file for complete search history.

(56) References Cited

U.S. PATENT DOCUMENTS 5,832,450 A   11/1998  Myers et al.
(Continued)

FOREIGN PATENT DOCUMENTS

JP       2005-237441 A    9/2005
(Continued)

OTHER PUBLICATIONS

USPTO office action for U.S. Appl. No. 12/169,402 (END920080098US1) dated Oct. 28, 2010.

(Continued)

*Primary Examiner* — Rodney Fuller
(74) *Attorney, Agent, or Firm* — Yee & Associates, P.C.; John R. Pivnichny

(57) ABSTRACT

A computer implemented method, apparatus, and computer program product for determining the efficacy of neuropsychiatric therapy is provided. A neuroimage mapping manager automatically compares a first set of regions of interest in a first set of scans taken at a first time to a second set of regions of interest in a second set of scans generated at a second time and identifies a set of changes in the regions of interest occurring over time. The neuroimage mapping manager searches a set of electronic medical literature sources for medical literature relevant to the set of changes in the regions of interest and identifies portions of the relevant medical literature associated with the set of changes in the regions of interest. The neuroimage mapping manager generates results comprising the set of changes in the regions of interest and a set of links to the portions of the relevant medical literature.

26 Claims, 6 Drawing Sheets

U.S. PATENT DOCUMENTS

| | | | |
|---|---|---|---|
| 5,845,255 | A | 12/1998 | Mayaud |
| 7,051,022 | B1* | 5/2006 | Faisal ................................. 1/1 |
| 7,844,560 | B2 | 11/2010 | Krishnan et al. |
| 7,996,242 | B2 | 8/2011 | Fueyo et al. |
| 2005/0038678 | A1* | 2/2005 | Qian et al. ....................... 705/2 |
| 2005/0043965 | A1 | 2/2005 | Heller et al. |
| 2005/0215889 | A1* | 9/2005 | Patterson, II ................. 600/436 |
| 2005/0244036 | A1* | 11/2005 | Rusinek et al. ............... 382/120 |
| 2006/0120584 | A1 | 6/2006 | Hillman |
| 2007/0276777 | A1 | 11/2007 | Krishnan et al. |
| 2009/0006061 | A1* | 1/2009 | Thukral et al. ................. 703/11 |
| 2009/0316968 | A1* | 12/2009 | Fueyo et al. .................. 382/131 |
| 2010/0010363 | A1* | 1/2010 | Fueyo et al. .................. 600/544 |
| 2010/0010827 | A1* | 1/2010 | Fueyo et al. ..................... 705/2 |
| 2010/0010831 | A1* | 1/2010 | Fueyo et al. ..................... 705/3 |

FOREIGN PATENT DOCUMENTS

| | | |
|---|---|---|
| JP | 2006-204641 A | 8/2006 |
| WO | 2007/063656 A1 | 6/2007 |

OTHER PUBLICATIONS

USPTO Notice of allowance for U.S. Appl. No. 12/169,402 dated Apr. 6, 2011.

U.S. Appl. No. 12/141,316, filed Jun. 18, 2008, Fueyo et al.

U.S. Appl. No. 12/169,339, filed Jul. 8, 2008, Fueyo et al.

U.S. Appl. No. 12/169,402, filed Jul. 8, 2008, Fueyo et al.

U.S. Appl. No. 12/169,329, filed Jul. 8, 2008, Fueyo et al.

U.S. Appl. No. 12/169,350, filed Jul. 8, 2008, Fueyo et al.

USPTO Office Action dated Jul. 7, 2011 for U.S. Appl. No. 12/169,329, (24 pages).

Barrett et al., "Regional CBF in chronic stable TBI treated with hyperbaric oxygen." Undersea & Hyperbaric Medicine; Winter 2004; 31, 4; ProQuest Health and Medical Complete, pp. 395-406.

* cited by examiner

DETERMINING EFFICACY OF THERAPEUTIC INTERVENTION IN NEUROSYCHIATRIC DISEASE

BACKGROUND OF THE INVENTION

1. Field of the Invention

The present invention is related generally to a data processing system and in particular to a method and apparatus for managing neuropsychiatric disease data. More particularly, the present invention is directed to a computer implemented method, apparatus, and computer usable program code for measuring the effectiveness of therapies in neuropsychiatric disease based on analysis of imaging data and literature.

2. Description of the Related Art

Neuropsychiatric disorders are disorders that have neurological features associated with disorders of the nervous system, as well as psychiatric features. Neuropsychiatric disorders may be treated using a variety of therapies, such as talk therapy, behavioral therapy, chemical therapy, and/or mechanical therapy. Chemical therapy refers to pharmacotherapy, such as, the utilization of drugs. Mechanical therapy includes electroconvulsive therapies (ECT). These therapies may be used separately or may be used in combination to treat patients diagnosed with neuropsychiatric disorders.

However, many of these patients may not receive the most effective treatments due to difficulties in accurately diagnosing patients with neuropsychiatric disorders. Patients that are accurately diagnosed may also suffer from the side effects of both effective therapies and trails of ineffective therapies. Furthermore, some patients may suffer for years as a result of poorly understood disease phenotype, particularly in cases involving the presentation of complex cases. In addition, when a disease is developing in a patient and the patient has not had a sufficient number of "episodes" for diagnosis or has only manifested a few early stage symptoms, it may be difficult or impossible to clearly and rapidly delineate a differential diagnosis.

BRIEF SUMMARY OF THE INVENTION

According to one embodiment of the present invention, a computer implemented method, apparatus, and computer program product for determining the efficacy of neuropsychiatric therapy is provided. The neuroimage mapping manager automatically compares a first set of regions of interest in a first set of scans taken at a first time to a second set of regions of interest in a second set of scans generated at a second time period. A region of interest is an area that shows an indication of a potential abnormality, an area that shows an indication of potential disease, or an area that is expected to change due to therapy. The neuroimage mapping manager identifies a set of changes in the regions of interest occurring over time based on the comparison of the first set of regions of interest to the second set of regions of interest. The neuroimage mapping manager searches a set of electronic medical literature sources for medical literature relevant to the set of changes in the regions of interest occurring over time to form relevant medical literature. The neuroimage mapping manager identifies portions of the relevant medical literature associated with the set of changes in the regions of interest. The neuroimage mapping manager generates neuroimage mapping results. The neuroimage mapping results comprises the set of changes in the regions of interest and a set of links to the portions of the relevant medical literature that are correlated to the regions of interest or the changes in the regions of interest.

In one embodiment, the set of links to the portions of the relevant medical literature may be embedded in the first set of changes in the regions of interest. In another embodiment, the set of links to the portions of the relevant medical literature are stored in an electronic copy of a medical file for the patient. The neuroimage mapping results may also include the first set of regions of interest and the second set of regions of interest.

In one embodiment, the set of baseline control scans comprises a set of baseline normal scans, a set of baseline abnormal scans, and/or a set of baseline treatment scans. The neuroimage mapping manager receives a set of brain scans for a set of healthy subjects in various demographic groups to form the baseline normal scans. The neuroimage mapping manager analyzes the baseline normal scans to identify a normal appearance of areas in normal brain scans, wherein a normal brain scan is a scan that does not show indications of disease or abnormalities in the areas in the normal brain scans. The neuroimage mapping manager may also receive a set of brain scans for a set of subjects in various demographic groups having identified abnormalities in the set of brain scans to form the baseline abnormal scans. The neuroimage mapping manager analyzes the baseline abnormal scans to identify an abnormal appearance of areas in brain scans. An abnormal scan is a scan that shows indications of disease or abnormalities in the areas of the brain scans. The neuroimage mapping manager may also receive a set of brain scans for a set of subjects in various demographic groups having identified conditions and undergoing identified therapies or treatments to form the baseline treatment scans. The neuroimage mapping manager analyzes the baseline treatment scans to identify an appearance of areas in brain scans during a course of at least one identified therapy or treatment. A treatment scan is a scan that shows effects of treatments or therapies in the areas of the brain scans.

In another embodiment, the neuroimage mapping manager correlates clinical data for the patient to the set of changes in the regions of interest. The results comprise a set of links to portions of the clinical data for the patient corresponding to the changes in the regions of interest in the set of scans for the patient.

In response to a determination that the set of changes in the regions of interest indicates a change in brain chemistry or brain metabolism, the neuroimage mapping manager may determine a location of the change in brain chemistry or a location of the change in brain metabolism in the set of scans for the patient and identify an amount of change in the brain chemistry or the brain metabolism. The set of changes in the areas of interest in this embodiment may include an identification of the location of the change in brain chemistry and brain metabolism and an indication of a degree of change in the brain chemistry and brain metabolism.

In another embodiment, in response to a determination that the set of changes in the regions of interest indicates a change in brain chemistry or brain metabolism, the neuroimage mapping manager determines whether the change in brain chemistry or brain metabolism correlates with clinical data for the patient. The neuroimage mapping manager identifies correlations between the changes in the brain chemistry and brain metabolism with the clinical data in the results.

DETAILED DESCRIPTION OF THE INVENTION

Figure 1:
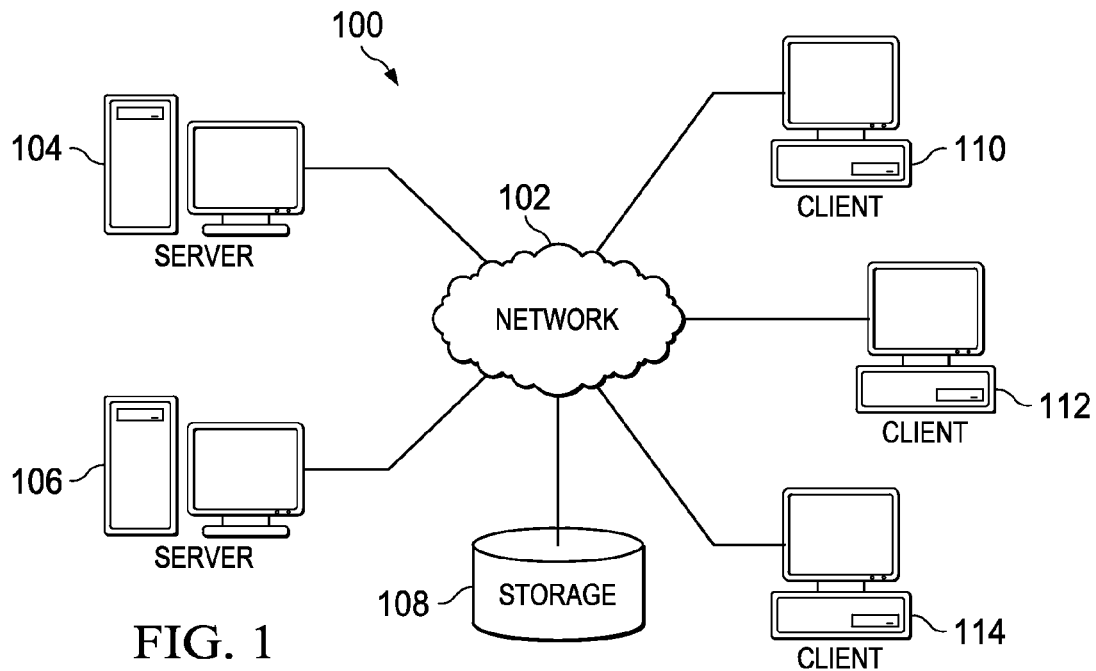
FIG. 1 is a pictorial representation of a network of data processing systems in which illustrative embodiments may be implemented.

As will be appreciated by one skilled in the art, the present invention may be embodied as a system, method or computer program product. Accordingly, the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, the present invention may take the form of a computer program product embodied in any tangible medium of expression having computer usable program code embodied in the medium.

Any combination of one or more computer usable or computer readable medium(s) may be utilized. The computer-usable or computer-readable medium may be, for example but not limited to, an electronic, magnetic, optical, electromagnetic, infrared, or semiconductor system, apparatus, or device. More specific examples (a non-exhaustive list) of the computer-readable medium would include the following: a portable computer diskette, a hard disk, a random access memory (RAM), a read-only memory (ROM), an erasable programmable read-only memory (EPROM or Flash memory), a portable compact disc read-only memory (CDROM), an optical storage device, or a magnetic storage device. Note that the computer-usable or computer-readable medium could even be paper or another suitable medium upon which the program is printed, as the program can be electronically captured, via, for instance, optical scanning of the paper or other medium, then compiled, interpreted, or otherwise processed in a suitable manner, if necessary, and then stored in a computer memory. In the context of this document, a computer-usable or computer-readable medium may be any medium that can contain, store, or physically transport the program for use by or in connection with the instruction execution system, apparatus, or device.

Computer program code for carrying out operations of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

The present invention is described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions.

These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer program instructions may also be stored in a computer-readable medium that can direct a computer or other programmable data processing apparatus to function in a particular manner, such that the instructions stored in the computer-readable medium produce an article of manufacture including instruction means which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide processes for implementing the functions/acts specified in the flowchart and/or block diagram block or blocks.

FIG. 1 depicts a pictorial representation of a network of data processing systems in which illustrative embodiments may be implemented. Network data processing system 100 is a network of computers in which the illustrative embodiments may be implemented. Network data processing system 100 contains network 102, which is the medium used to provide communications links between various devices and computers connected together within network data processing system 100. Network 102 may include connections, such as wire, wireless communication links, or fiber optic cables.

In the depicted example, server 104 and server 106 connect to network 102 along with storage unit 108. In addition, clients 110, 112, and 114 connect to network 102. Clients 110, 112, and 114 may be, for example, personal computers or network computers. In the depicted example, server 104 provides data, such as boot files, operating system images, and applications to clients 110, 112, and 114. Clients 110, 112, and 114 are clients to server 104 in this example. Network data processing system 100 may include additional servers, clients, and other devices not shown.

In the depicted example, network data processing system 100 is the Internet with network 102 representing a worldwide collection of networks and gateways that use the Transmission Control Protocol/Internet Protocol (TCP/IP) suite of protocols to communicate with one another. At the heart of the Internet is a backbone of high-speed data communication lines between major nodes or host computers, consisting of thousands of commercial, governmental, educational and other computer systems that route data and messages. Of course, network data processing system 100 also may be implemented as a number of different types of networks, such as for example, an intranet, a local area network (LAN), or a wide area network (WAN). FIG. 1 is intended as an example, and not as an architectural limitation for the different illustrative embodiments.

Figure 2:
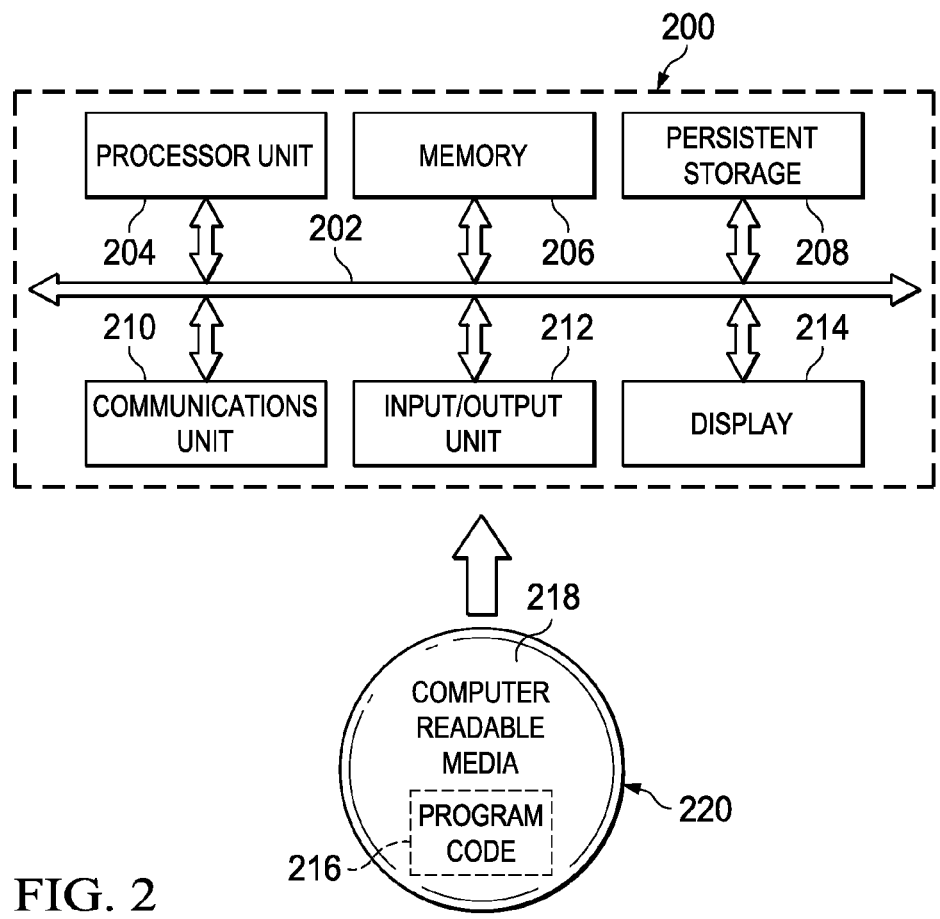
FIG. 2 is a block diagram of a data processing system in which illustrative embodiments may be implemented.

With reference now to FIG. 2, a block diagram of a data processing system is shown in which illustrative embodiments may be implemented. Data processing system 200 is an example of a computer, such as server 104 or client 110 in FIG. 1, in which computer usable program code or instructions implementing the processes may be located for the illustrative embodiments. In this illustrative example, data processing system 200 includes communications fabric 202, which provides communications between processor unit 204, memory 206, persistent storage 208, communications unit 210, input/output (I/O) unit 212, and display 214.

Processor unit 204 serves to execute instructions for software that may be loaded into memory 206. Processor unit 204 may be a set of one or more processors or may be a multi-processor core, depending on the particular implementation. Further, processor unit 204 may be implemented using one or more heterogeneous processor systems in which a main processor is present with secondary processors on a single chip. As another illustrative example, processor unit 204 may be a symmetric multi-processor system containing multiple processors of the same type.

Memory 206 and persistent storage 208 are examples of storage devices. A storage device is any piece of hardware that is capable of storing information either on a temporary basis and/or a permanent basis. Memory 206, in these examples, may be, for example, a random access memory or any other suitable volatile or non-volatile storage device. Persistent storage 208 may take various forms depending on the particular implementation. For example, persistent storage 208 may contain one or more components or devices. For example, persistent storage 208 may be a hard drive, a flash memory, a rewritable optical disk, a rewritable magnetic tape, or some combination of the above. The media used by persistent storage 208 also may be removable. For example, a removable hard drive may be used for persistent storage 208.

Communications unit 210, in these examples, provides for communications with other data processing systems or devices. In these examples, communications unit 210 is a network interface card. Communications unit 210 may provide communications through the use of either or both physical and wireless communications links.

Input/output unit 212 allows for input and output of data with other devices that may be connected to data processing system 200. For example, input/output unit 212 may provide a connection for user input through a keyboard and mouse. Further, input/output unit 212 may send output to a printer. Display 214 provides a mechanism to display information to a user.

Instructions for the operating system and applications or programs are located on persistent storage 208. These instructions may be loaded into memory 206 for execution by processor unit 204. The processes of the different embodiments may be performed by processor unit 204 using computer implemented instructions, which may be located in a memory, such as memory 206. These instructions are referred to as program code, computer usable program code, or computer readable program code that may be read and executed by a processor in processor unit 204. The program code in the different embodiments may be embodied on different physical or tangible computer readable media, such as memory 206 or persistent storage 208.

Program code 216 is located in a functional form on computer readable media 218 that is selectively removable and may be loaded onto or transferred to data processing system 200 for execution by processor unit 204. Program code 216 and computer readable media 218 form computer program product 220 in these examples. In one example, computer readable media 218 may be in a tangible form, such as, for example, an optical or magnetic disc that is inserted or placed into a drive or other device that is part of persistent storage 208 for transfer onto a storage device, such as a hard drive that is part of persistent storage 208. In a tangible form, computer readable media 218 also may take the form of a persistent storage, such as a hard drive, a thumb drive, or a flash memory that is connected to data processing system 200. The tangible form of computer readable media 218 is also referred to as computer recordable storage media. In some instances, computer recordable media 218 may not be removable.

Alternatively, program code 216 may be transferred to data processing system 200 from computer readable media 218 through a communications link to communications unit 210 and/or through a connection to input/output unit 212. The communications link and/or the connection may be physical or wireless in the illustrative examples. The computer readable media also may take the form of non-tangible media, such as communication links or wireless transmissions containing the program code.

The different components illustrated for data processing system 200 are not meant to provide architectural limitations to the manner in which different embodiments may be implemented. The different illustrative embodiments may be implemented in a data processing system including components in addition to or in place of those illustrated for data processing system 200. Other components shown in FIG. 2 can be varied from the illustrative examples shown.

As one example, a storage device in data processing system 200 is any hardware apparatus that may store data. Memory 206, persistent storage 208, and computer readable media 218 are examples of storage devices in a tangible form.

In another example, a bus system may be used to implement communications fabric 202 and may be comprised of one or more buses, such as a system bus or an input/output bus. Of course, the bus system may be implemented using any suitable type of architecture that provides for a transfer of data between different components or devices attached to the bus system. Additionally, a communications unit may include one or more devices used to transmit and receive data, such as a modem or a network adapter. Further, a memory may be, for example, memory 206 or a cache such as found in an interface and memory controller hub that may be present in communications fabric 202.

According to one embodiment of the present invention, a computer implemented method, apparatus, and computer program product for determining the efficacy of neuropsychiatric therapy is provided. The neuroimage mapping manager automatically compares a first set of regions of interest in a first set of scans taken at a first time to a second set of regions of interest in a second set of scans generated at a second time period. The scans may be, without limitation, magnetic resonance imaging scans or positron emission tomography scans of a human brain. In addition, the second time is a different time than the first time. The second time may be a given period of time after the first time. For example, the second time may be a day, a week, a month, or a year after the first time.

Unless otherwise indicated, the term "set" refers to one or more. Therefore, a set of regions of interest may include a single region of interest, as well as two or more regions of interest. A region of interest is an area that shows an indication of a potential abnormality, an area that shows an indication of potential disease, or an area that is expected to change due to therapy.

The neuroimage mapping manager identifies a set of changes in the regions of interest occurring over time based on the comparison of the first set of regions of interest to the second set of regions of interest. The neuroimage mapping manager searches a set of electronic medical literature sources for medical literature relevant to the set of changes in the regions of interest occurring over time to form relevant medical literature. The neuroimage mapping manager identifies portions of the relevant medical literature associated with the set of changes in the regions of interest. The neuroimage mapping manager generates neuroimage mapping results. The neuroimage mapping results comprises the set of changes in the regions of interest and a set of links to the portions of the relevant medical literature that are correlated to the regions of interest or the changes in the regions of interest.

Figure 3:
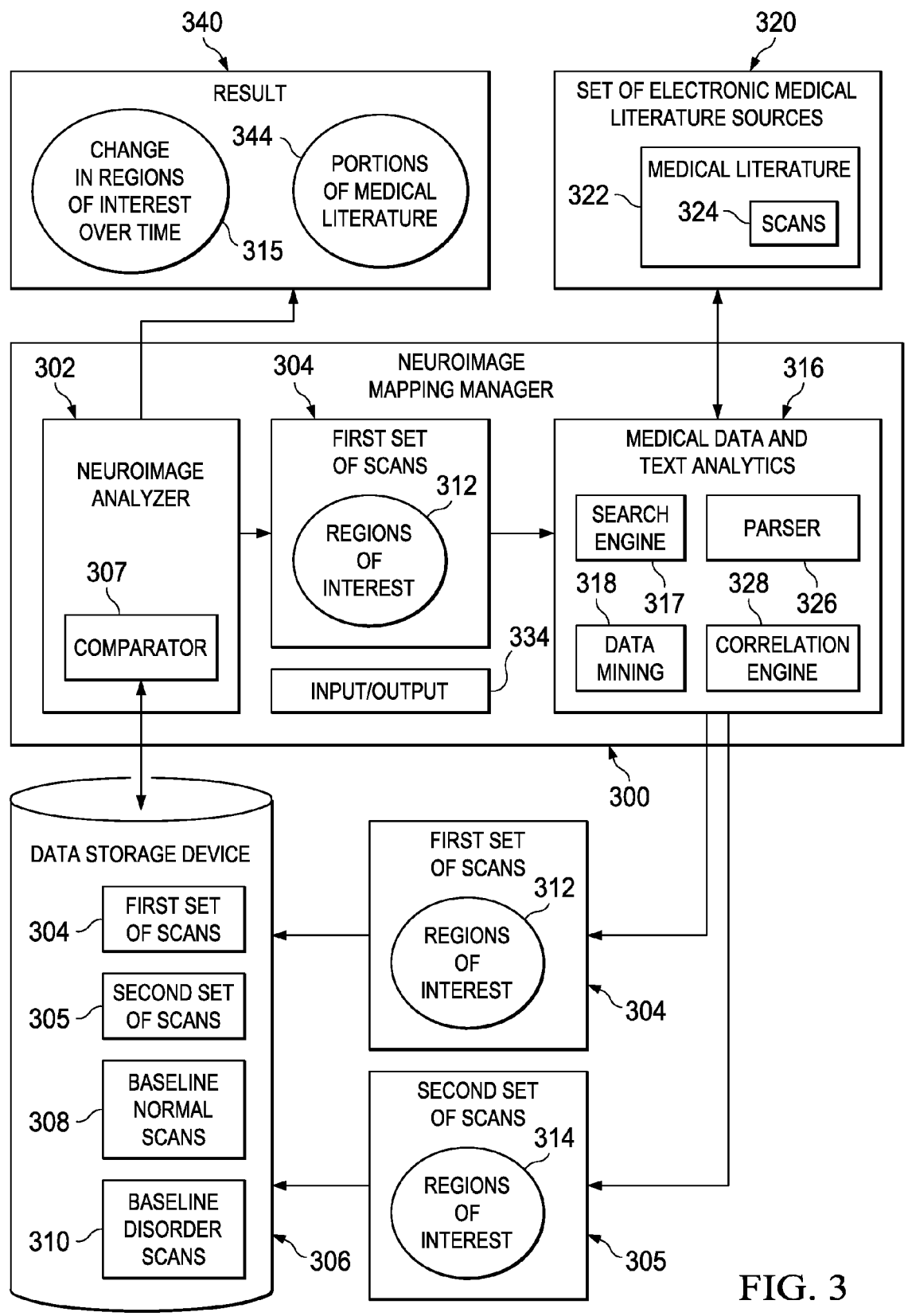
FIG. 3 is a block diagram of a neuroimage mapping manager in accordance with an illustrative embodiment.

FIG. 3 is a block diagram of a neuroimage mapping manager in accordance with an illustrative embodiment. Neuroimage mapping manager 300 is software for analyzing patient brain scans to identify regions of interest in the brain scans and generate links to portions of interest in the medical literature. Neuroimage mapping manager 300 may be implemented in any type of computing device, such as, without limitation, a server, a client, a laptop computer, a personal digital assistant (PDA), a smart phone, or any other known or available computing device.

Neuroimage analyzer 302 receives first set of scans 304. First set of scans 304 is a set of one or more brain scans that are generated at a first time period. The first time period may be a time period prior to beginning one or more therapies or a time period occurring after one or more therapies have begun. First set of scans 304 may include functional magnetic resonance imaging (fMRI) scans, structural magnetic resonance imaging (sMRI) scans, positron emission tomography (PET) scans, or any other type of brain scans. Neuroimage analyzer 302 also receives second set of scans 305. Second set of scans 305 are generated at a second time period. The second time period is a time period after the first time period. For example, and without limitation, if the first time period occurs prior to beginning a therapy, the second time period may be, without limitation, one month, six months, or one year after the therapy was initiated at the first time period.

The scans in first set of scans 304 and second set of scans may be generated by one or more scanning devices. The scanning devices may be implemented as one or more of a functional magnetic resonance imaging device, a structural magnetic resonance imaging device, a positron emission tomography device, or any other type of device for generating scans of a brain, such as a human patient's brain. A patient is not limited to a patient admitted in a hospital. The term patient may refer to any person obtaining medical care, consulting a medical practitioner, participating in a medical study, obtaining medical advice, or otherwise participating in medical tests and/or medical procedures. The one or more scanning devices may save the scans of the patient's brain in data storage device 306.

Data storage device 306 may be implemented as a hard drive, a flash memory, a main memory, read only memory (ROM), a random access memory (RAM), or any other type of data storage device. Data storage may be implemented in a single data storage device or a plurality of data storage devices.

Neuroimage analyzer 302 may receive the scans in first set of scans 304 and/or second set of scans 305 from the one or more scanning devices as each scan is generated, or neuroimage analyzer 302 may retrieve the scans from a pre-generated set of scans stored in data storage device 306. Neuroimage analyzer 302 analyzes first set of scans 304 to identify regions of interest in the scans based on baseline normal scans and/or baseline disorder scans for identified illnesses, abnormalities, diseases, disorders, or other known conditions.

A region of interest is an area in a scan that shows an indication of a potential abnormality, a potential illness, a potential disease, a potential condition, or any other deviation from what would be expected in a scan of the region for a healthy individual having similar characteristics as the patient. The similar characteristics may include, without limitation, an age range of the patient, race, gender, or other factors influencing the development and appearance of regions of the brain in a scan.

Comparator 307 is a software component that compares first set of scans 304 to baseline normal scans 308 and/or baseline abnormal scans 310 to identify regions of interest 312. Comparator 307 compares each scan in second set of scans with baseline normal scans 308, baseline disorder scans 310, and/or regions of interest 312 in first set of scans 304 to identify regions of interest 314 in second set of scans 305.

Baseline normal scans 308 may include, without limitation, a set of one or more brain scans for average, healthy subjects having one or more characteristics in common with the patient. The characteristics in common may be age, gender, race, pre-existing conditions, profession, place of residence, nationality, or any other characteristic. For example, if the patient is a sixteen year old female, baseline normal scans 308 may include scans of normal, healthy female subjects between the ages of fourteen and eighteen. Comparator 307 compares one or more areas in each scan in first set of scans 304 with corresponding areas in one or more scans in baseline normal scans 308 to identify areas of the patient's scans that are consistent with the scans of normal, healthy subjects and to identify areas of the scans that are inconsistent with the scans of normal, healthy subjects. An area in a scan that is inconsistent with the corresponding areas in baseline normal scans 308 are identified as regions of interest 312. A region identified in regions of interest 312 may indicate a potential abnormality, illness, or condition. However, each region in regions of interest 312 are not required to definitively indicate an abnormality, illness, condition, or other deviation from the norm.

Baseline abnormal scans 310 is a set of one or more scans of subjects having one or more characteristics in common with the patient and diagnosed with an identified condition. The identified condition may be a disease, an illness, a deformity, an abnormality, or any other identified deviation from the norm. For example, if the patient is a male, age thirty five, and diagnosed with diabetes, the baseline abnormal scans may include scans of male patients between the ages of thirty and forty and having a variety of known neuropsychiatric disorders. Comparator 307 compares regions in each scan in patient set of scans 304 with one or more scans in baseline abnormal scans 310 to identify regions of interest in the patient's scans that show indications of neuropsychiatric disorders, illness, disease, or abnormalities. A region in a scan may show indications of a potential illness, condition, abnormality, or neuropsychiatric disorder if the region in the patient's scan is consistent with a corresponding region in a brain scan of a subject having a known illness, condition, abnormality, or neuropsychiatric disorder. Comparator 307 also compares regions of interest 312 in first set of scans 304 with regions of interest 314 in second set of scans 305 to identify one or more changes in the regions of interest over time 315.

Medical data and text analytics 316 is a software component for searching a set of electronic medical literature sources for medical literature relevant to regions of interest 312 in first set of scans 304, regions of interest 314 in second set of scans 305, and changes in regions of interest over time 315. Medical data and text analytics 316 correlates portions of the relevant medical literature describing regions of interest 312, regions of interest 314, and/or change in regions of interest over time 315.

Search engine 317 is any type of known or available information retrieval software for locating medical literature that is relevant to regions of interest 312, regions of interest 314, and/or change in regions of interest over time 315 in one or more sources of medical literature. Search engine 317 may be software for searching data storage devices on a computer system or a web search tool for searching for medical information on the World Wide Web. Search engine 317 may also make queries into databases, information systems, and other medical literature information sources to locate information relevant to regions of interest 312, regions of interest 314, and/or change in regions of interest over time 315. Data mining 318 is a software tool for searching through information available from one or more sources and retrieving medical information relevant to regions of interest 312, regions of interest 314, and/or change in regions of interest over time 315.

Searching through the information from one or more sources may include, without limitation, using at least one of data mining, search engines, pattern recognition, queries to identify the relevant medical literature in the medical literature available from the set of electronic medical literature sources, data mining cohort, pattern recognition cohort, search engine cohort, or any other cohort appliance of interest. A cohort is a group of one or more objects having a common characteristic. For example, a data mining cohort may be, without limitation, a group of one or more objects associated with performing data mining techniques to identify desired data from a data source. A pattern recognition cohort may be, without limitation, a group of pattern recognition software applications that identify patterns in data, such as medical data.

Data mining 318, search engine 317, or any other software for locating relevant information may be used to search set of electronic medical literature sources 320 for relevant medical literature. Set of electronic medical literature sources 320 may include both online medical literature sources that are accessed by neuroimage mapping manager 300 via a network connection, as well as off-line medical literature sources that may be accessed without a network connection. An example of an electronic medical literature source includes, without limitation, PUBMED. Medical literature 322 is any literature, journal article, medical study results, medical text, pharmaceutical studies, or any other medical information in an electronic format. Medical literature 322 may include scans 324, such as magnetic resonance imaging scans, positron emission tomography scans, or any other type of brain scans.

Parser 326 is software for parsing medical literature 322 text into a form suitable for further analysis and processing. Parser 326 may be implemented as any type of known or available parser. Correlation engine 328 correlates portions of medical literature 332 with regions of interest 312, regions of interest 314, and/or change in regions of interest over time 315. A portion of medical literature is a section of medical literature text and/or one or more scans that describes a region of interest, describes a condition, illness, deformity, abnormality, disease, or other cause for an appearance of a region of interest, an area in a scan that is the same or similar to an area of interest, or otherwise is associated with a region of interest.

Neuroimage mapping manager 300 generates result 340, including change in regions of interest over time 315 and portions of medical literature 344. Result 340 may optionally include an identification of regions of interest 312 in first set of scans 304 and/or regions of interest 314 in second set of scans 305. Change in regions of interest over time 315 may be output with a set of links to portions of medical literature 344 embedded in change in regions of interest over time 315. The set of links to portions of medical literature 344 may also optionally be embedded in first set of scans 304 or embedded within regions of interest 312 in first set of scans. The set of links to portions of medical literature 344 may also optionally be embedded in second set of scans 305 or be embedded within regions of interest 314 in second set of scans.

In another embodiment, links to portions of medical literature 344 may be output in result 340 separately from regions of interest 312, regions of interest 314, and/or change in regions of interest over time 315. In another embodiment, the set of links to portions of medical literature 344 are embedded in an electronic medical file for the patient or a file for brain scan results for one or more patients. A user selects a link in the set of links to view a portion of medical literature associated with a region of interest. The portion of medical literature may be a scan only, text only, or a combination of text and one or more scans. The portion of medical literature may be an entire or complete item, such as a complete medical journal article or a complete section of a medical textbook. The portion of medical literature may also be a portion of a journal article, a portion of a section of a medical textbook, or other part of an item of medical literature.

In this embodiment, baseline normal scans 308 and baseline abnormal scans 310 are pre-generated and available for retrieval from data storage device 306. However, in another embodiment, medical data and text analytics 314 searches set of electronic medical literature sources 320 for scans of normal, healthy subjects to create baseline normal scans 308. Medical data and text analytics 316 also searches set of medical literature sources 320 for scans of subjects having known abnormalities, deformities, illnesses, ailments, diseases, or other neuropsychiatric disorders to create baseline abnormal scans 310.

Thus, neuroimage mapping manager 300 provides data and text analytics to automatically determine regions of a patient's brain affected by disease as depicted in functional neuroimaging data, such as functional magnetic resonance imaging and positron emission tomography. Neuroimage mapping manager 300 applies technologies to data, such as heuristics, which automatically correlate the changes in affected brain regions over time with text in medical literature 322 that describes the changes in regions of interest 312 and 314 found in both functional and structural data in patient set of scans 304.

Input/output 334 may be implemented as any type of input and/or output device for presenting regions of interest 312 and/or 314 to a user and/or receiving a selection of one or more regions from a user. In other words, neuroimage analyzer 302 automatically identifies one or more regions of interest in patient set of scans 304. Neuroimage analyzer 302 may optionally present the automatically selected regions of interest to the user using input/output 334. The automatically selected regions of interest may be presented using a display device to present the regions of interest in a visual format, using an audio device to present the regions of interest to the user in an audio format, using a combination of audio and visual devices, or any other presentation device.

The user may utilize input/output 334 to choose to select one or more additional regions of interest in patient set of scans 304. In such a case, neuroimage analyzer 302 adds the manually selected set of one or more regions of interest to regions of interest 312. In one embodiment, the regions of interest that are not automatically selected by neuroimage analyzer 302 and/or the user are automatically removed by neuroimage analyzer 302. In another embodiment, the user may choose to de-select or remove one or more regions of interest that were automatically selected by neuroimage analyzer 302. In such a case, neuroimage analyzer 302 automatically removes the one or more regions of interest selected for removal by the user from regions of interest 312.

In another embodiment, neuroimage mapping manager 300 makes a determination as to whether changes in regions of interest over time 315 correlate with the patient's clinical data. Clinical data is data describing the results of clinical laboratory tests. Clinical data describes the presence of substances in the blood, urine, tissue, and body fluids. Clinical data may be relevant to diagnosis or therapy for a particular condition. Moreover, clinical data may reveal causes of one or more features in the brain scans. For example, clinical tests may indicate mercury poisoning or other substances in the blood that may be responsible for the changes in brain chemistry and/or brain function shown in the brain scans. Clinical data for a particular patient may be available on data storage device 306, obtained from a remote data storage device via a network connection, and/or may be manually input to neuroimage mapping manager through input/output device 334. If the changes in changes in regions of interest over time 315 correlate with the clinical data, neuroimage mapping manager 300 identifies the correlations in result 340. The correlations may be identified provided as information embedded within changes in regions of interest over time 315 or provided separately from change in regions of interest over time 315.

Figure 4:
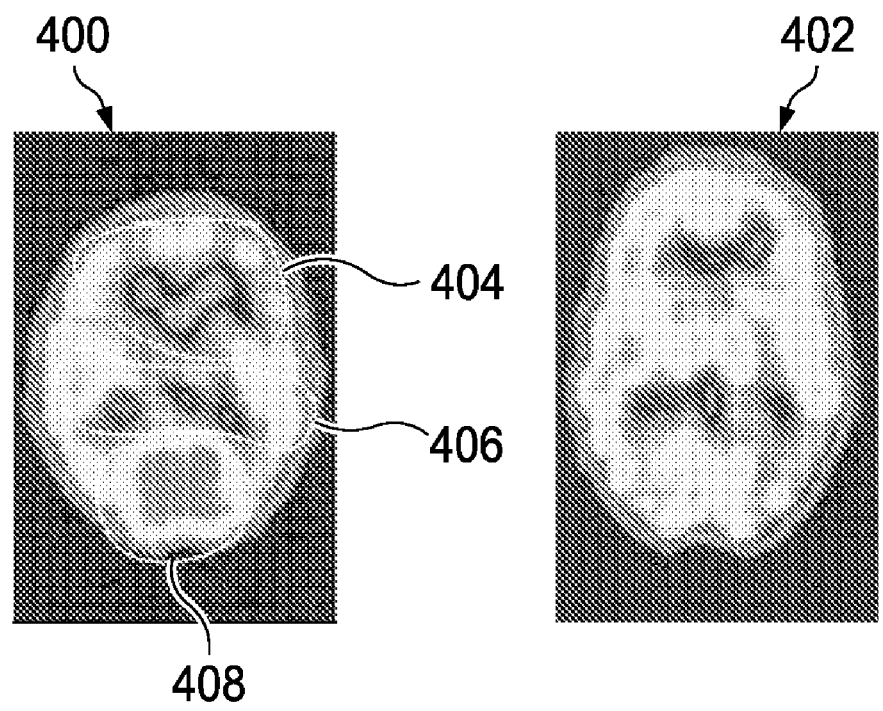
FIG. 4 is a block diagram of a magnetic resonance imaging brain scan having regions of interest in accordance with an illustrative embodiment.

Referring to FIG. 4, a block diagram of a magnetic resonance imaging brain scan having regions of interest is depicted in accordance with an illustrative embodiment. Scan 400 is a positron emission tomography scan of a brain of a patient. Scan 402 is a positron emission tomography scan of a normal, healthy subject. Scan 400 has regions of interest 404-408. Regions of interest 404-408 are areas in scan 400 that show indications of a potential condition, abnormality, chemical imbalance, illness, disease, or other deviation from an expected appearance of the scan. In this example, regions of interest 404-408 show disruptions in brain activity. Region 406 shows abnormal changes in the size of the ventricles of the brain. Region 408 shows decreased function in the frontal section.

Figure 5:
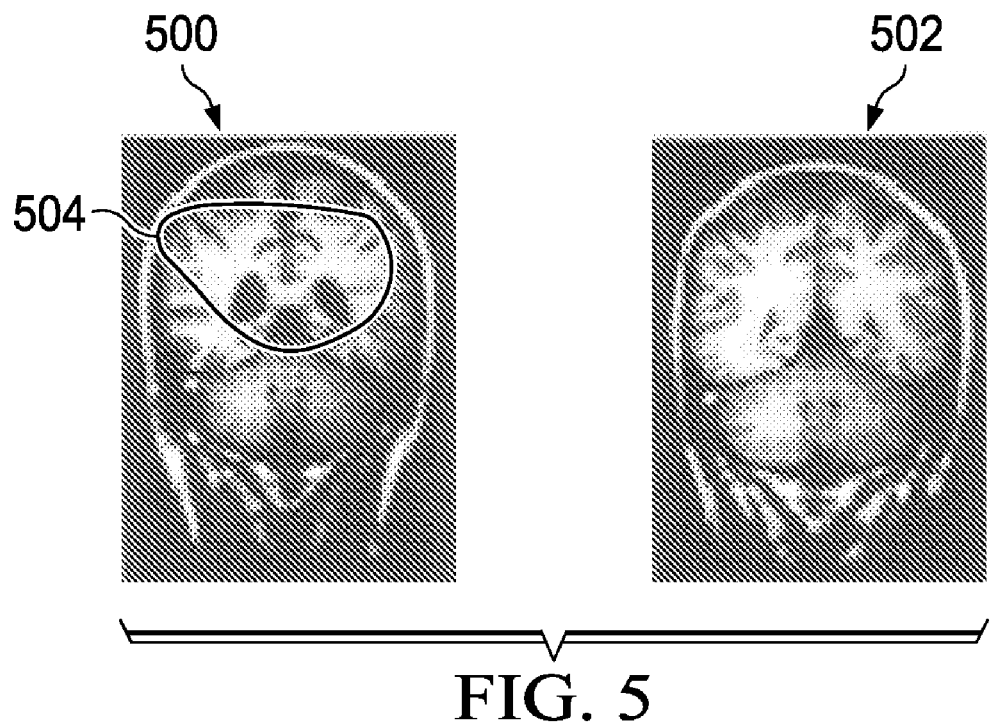
FIG. 5 is a positron emissions tomography brain scan having regions of interest in accordance with an illustrative embodiment.

Turning now to FIG. 5, a positron emissions tomography brain scan having regions of interest is shown in accordance with an illustrative embodiment. Scan 500 is a magnetic resonance imaging scan of a patient's brain. Scan 502 is a magnetic resonance imaging scan of a normal, healthy subject's brain. Scan 500 includes region of interest 504. Region 504 shows an enlargement of the ventricles of the brain when compared with scan 502 of a normal, healthy subject. The enlargement of the ventricles shown in region of interest 504 may indicate an illness or disease, such as, without limitation, schizophrenia. Therefore, a neuroimage mapping manager identifies region 504 as a region of interest.

Figure 6:
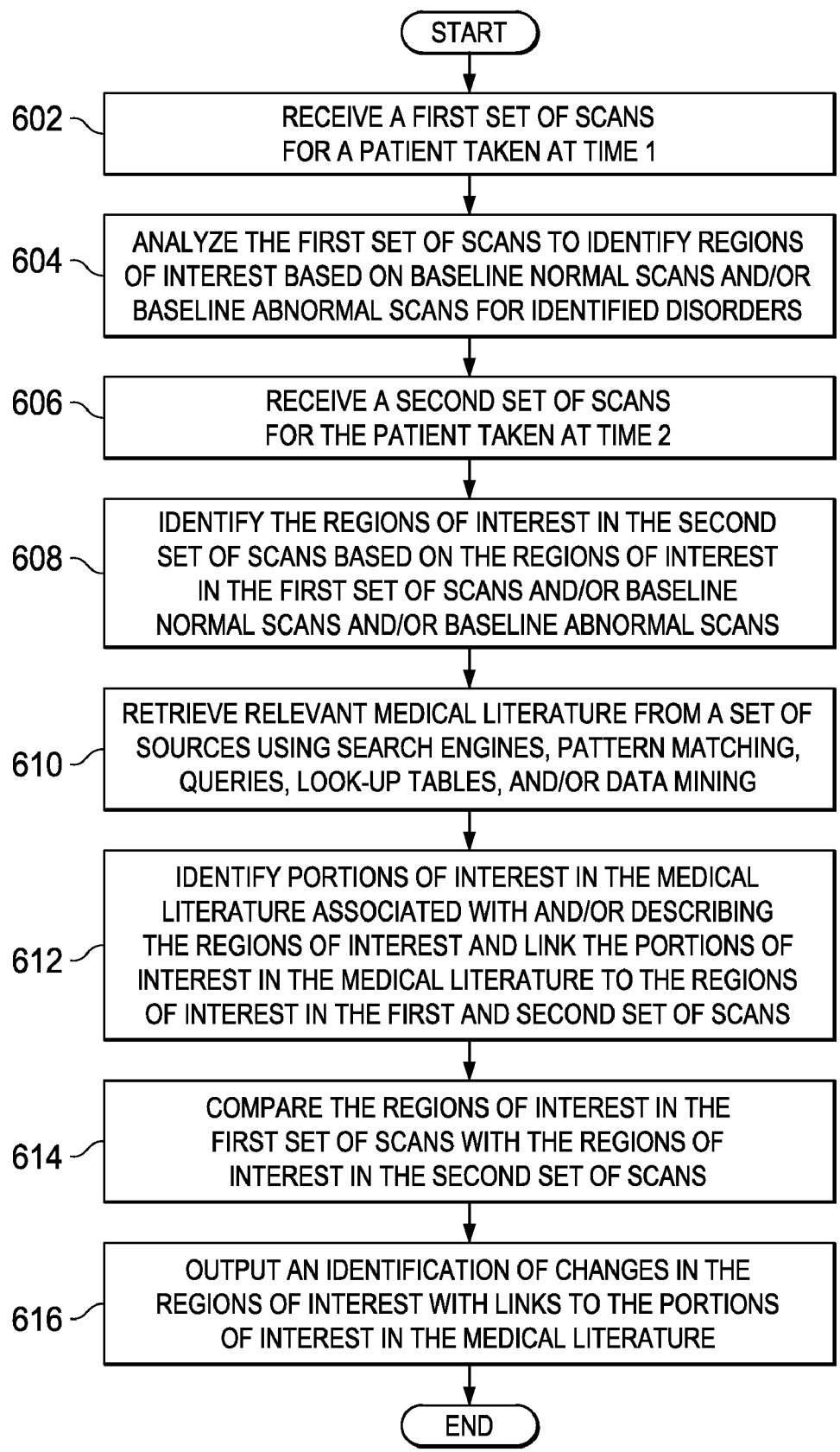
FIG. 6 is a flowchart illustrating a process for identifying changes in regions of interest in brain scans taken at different times and linking portions of interest in relevant medical literature with the regions of interest in the brain scans in accordance with an illustrative embodiment.

FIG. 6 is a flowchart illustrating a process for identifying changes in regions of interest in brain scans taken at different times and linking portions of interest in relevant medical literature with the regions of interest in the brain scans in accordance with an illustrative embodiment. The process in FIG. 6 may be implemented by software for identifying changes in regions of interest in patient scans and linking portions of the relevant medical literature, such as neuroimage analyzer 302 in FIG. 3.

The process begins by receiving a first set of scans for a patient taken at time one (step 602). The neuroimage analyzer analyzes the first set of scans to identify regions of interest based on baseline normal scans and/or baseline abnormal scans for identified disorders (step 604). The neuroimage analyzer receives a second set of scans for the patient taken at time two (step 606). The neuroimage analyzer identifies the regions of interest in the second set of scans based on the regions of interest in the first set of scans and/or baseline normal scans and/or baseline abnormal scans (step 608). The neuroimage analyzer retrieves relevant medical literature from a set of sources using search engines, pattern matching, queries, look-up tables, and/or data mining (step 610).

The neuroimage analyzer then identifies portions of interest in the medical literature associated with and/or describing the regions of interest and link the portions of interest in the medical literature to the regions of interest in the medical literature to the regions of interest in the first and second set of scans (step 612). The neuroimage analyzer compares the regions of interest in the first set of scans with the regions of interest in the second set of scans (step 614). The neuroimage analyzer outputs an identification of changes in the regions of interest with links to the portions of interest in the medical literature (step 616) with the process terminating thereafter.

Figure 7:
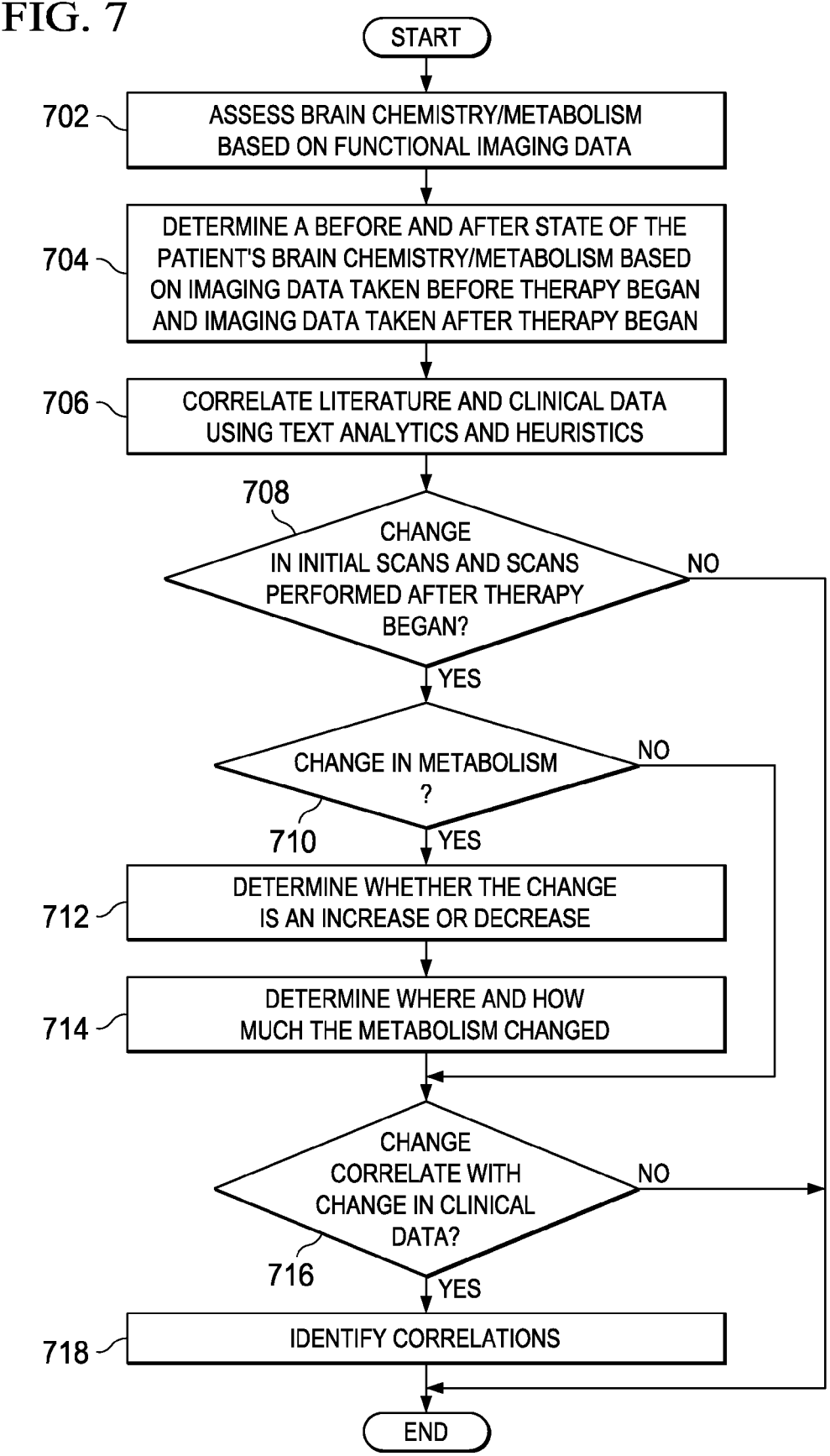
FIG. 7 is a flowchart illustrating a process for correlating changes in brain scans with medical literature and clinical data in accordance with an illustrative embodiment.

FIG. 7 is a flowchart illustrating a process for correlating changes in brain scans with medical literature and clinical data in accordance with an illustrative embodiment. The process in FIG. 7 may be implemented by software for correlating medical literature and clinical data with changes in regions of interest in brain scans occurring over time, such as neuroimage mapping manager 300 in FIG. 3.

The neuroimage mapping manager assesses brain chemistry and/or brain metabolism based on functional imaging data (step 702). The functional imaging data may be obtained from functional magnetic resonance imaging scans, positron emission tomography scans, or any other type of brain scan. The neuroimage mapping manager determines a before and after state of the patient's brain chemistry and/or brain metabolism based on imaging data taken before therapy began and imaging data taken after therapy began (step 704). The before and after state may be determined by comparing any first set of brain scans taken at a first time period with a second set of brain scans taken at a second time period. For example, and without limitation, the first set of brain scans may be taken prior to beginning therapy or at any point after beginning therapy and the second set of scans may be taken at a time period that is after the time period when the first set of scans were taken. In another example, the second set of scans may be taken a given period of time after the first set of scans, regardless of when therapy began. The second set of scans may be taken, without limitation, a week after the first set of scans, a month after the first set of scans, six months after the first set of scans, a year after the first set of scans, or any other period of time after the first set of scans were generated.

The neuroimage mapping manager correlates the before and after state of the patient's brain chemistry and/or brain metabolism to medical literature and clinical data for the patient using text analytics and heuristics (step 706). The neuroimage mapping manager makes a determination as to whether changes in the initial scans and scans performed after therapy began are present (step 708). If there are changes between the initial scans and the second set of scans performed after therapy began, the neuroimage mapping manager makes a determination as to whether the change is a change in metabolism (step 710). If the change is a change in metabolism, the neuroimage mapping manager determines whether the change is an increase or decrease (step 712). The neuroimage mapping manager then determines where the change occurred and how much the patient's brain metabolism changed (step 714).

The neuroimage mapping manager then makes a determination as to whether the changes correlate with the patient's clinical data (step 716). If the changes correlate with the clinical data, the neuroimage mapping manager identifies the correlations (step 718) with the process terminating thereafter. The correlations may be identified in the results identifying the regions of interest and the changes in the regions of interest from the initial set of scans to the second set of scans.

Figure 8:
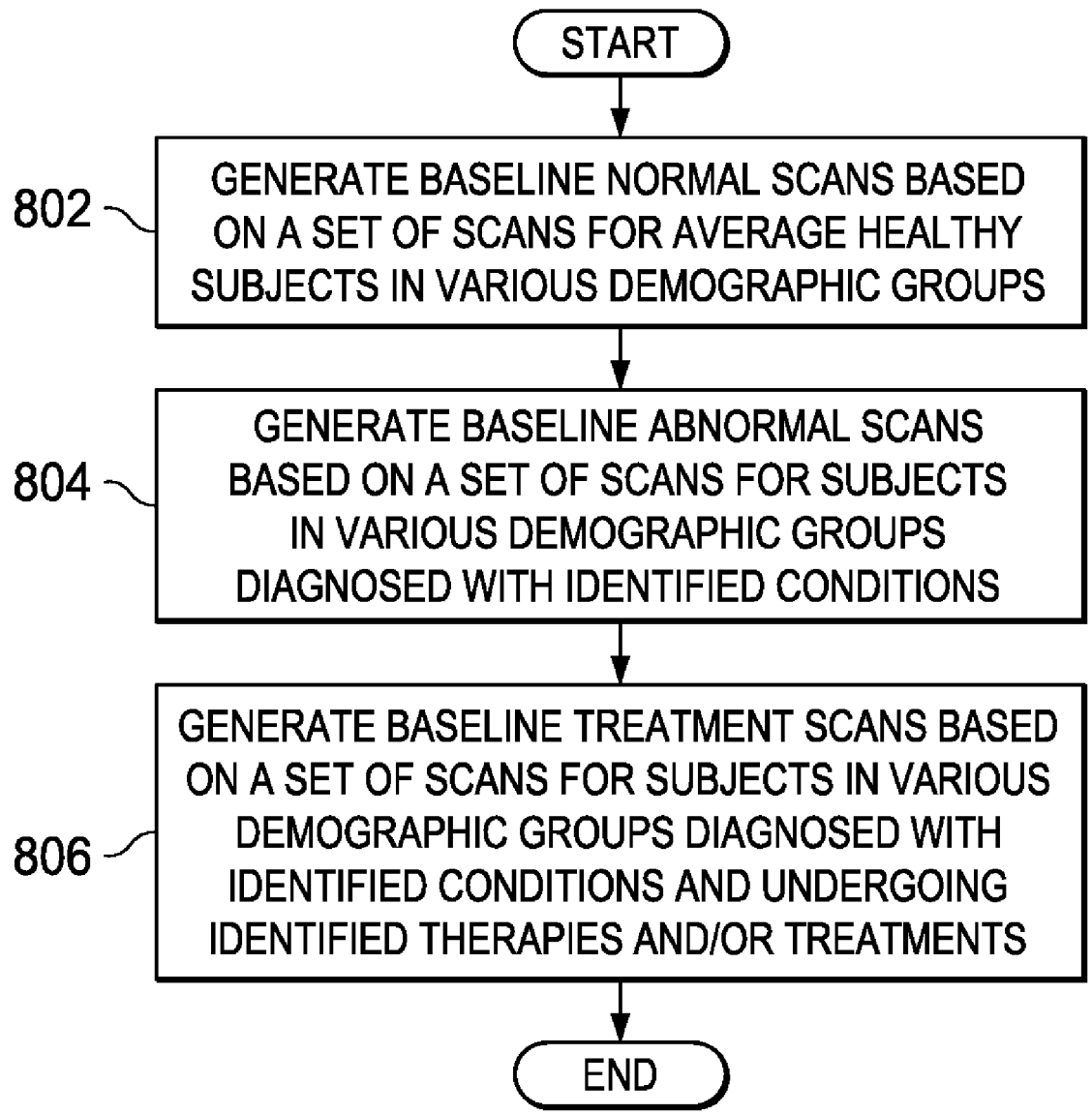
FIG. 8 is a flowchart illustrating a process for generating baseline control scans in accordance with an illustrative embodiment.

FIG. 8 is a flowchart illustrating a process for generating baseline control scans in accordance with an illustrative embodiment. The process in FIG. 8 may be implemented by software for generating a set of baseline control scans, such as medical data and text analytics 314 in FIG. 3.

The process begins by generating baseline normal scans based on a set of scans for average healthy subjects in various demographic groups (step 802). The medical data and text analytics may obtain the set of scans for the healthy subjects by searching a set of medical literature sources for the scans of normal, healthy subjects. The scans of the normal, healthy subjects may be saved in a data storage device to form baseline normal scans.

The medical data and text analytics generates baseline abnormal scans based on a set of scans for subjects in various demographic groups diagnosed with identified conditions (step 804). The medical data and text analytics may obtain the set of scans for subjects with the identified conditions by searching the set of medical literature sources for scans of subjects having known and/or diagnosed conditions. The conditions may be a disease, an illness, an infection, a deformity, or any other condition. The scans of the subjects having the known conditions may be saved in the data storage device to form baseline abnormal scans. The medical data and text analytics generates baseline treatment scans based on a set of scans for subjects in various demographic groups diagnosed with identified conditions and undergoing identified therapies and/or treatment (step 806) with the process terminating thereafter.

According to one embodiment of the present invention, a computer implemented method, apparatus, and computer program product for determining the efficacy of neuropsychiatric therapy is provided. The neuroimage mapping manager automatically compares a first set of regions of interest in a first set of scans taken at a first time to a second set of regions of interest in a second set of scans generated at a second time period. A region of interest is an area that shows an indication of a potential abnormality, an area that shows an indication of potential disease, or an area that is expected to change due to therapy. The neuroimage mapping manager identifies a set of changes in the regions of interest occurring over time based on the comparison of the first set of regions of interest to the second set of regions of interest. The neuroimage mapping manager searches a set of electronic medical literature sources for medical literature relevant to the set of changes in the regions of interest occurring over time to form relevant medical literature. The neuroimage mapping manager identifies portions of the relevant medical literature associated with the set of changes in the regions of interest. The neuroimage mapping manager generates neuroimage mapping results. The neuroimage mapping results comprises the set of changes in the regions of interest and a set of links to the portions of the relevant medical literature that are correlated to the regions of interest or the changes in the regions of interest.

The neuroimage mapping manager automates the assessment of neuroimage data and literature to detect and document whether a condition is present and/or whether a disease process may be occurring. The neuroimage mapping manager also identifies changes in regions of interest over time such that a determination can be made as to whether a patient's condition is improving, whether a patient's condition is becoming worse, whether therapy is effective or ineffective, whether a patient is responding to prescribed drugs, and/or whether a recovery process is progressing as anticipated. The neuroimage mapping manager automates the determination of regions of interest in brain scans via mapping of literature into the brain scans and improves the speed and potentially the accuracy of diagnostic and treatment processes. For instance, the neuroimage mapping manager may put a map of the portions of relevant medical literature onto a patient's scans for the diagnostic measurement of drug and/or treatment efficacy.

The neuroimage mapping manager automates the determination of efficacy of therapy via a determination of whether brain metabolism is normalizing as depicted via neuroimage data and/or portions of the relevant medical literature. The neuroimage mapping manager may also make a determination as to whether treatment is having a desired effect as depicted via clinical symptoms correlated with the imaging data in the brain scans generated over time.

The neuroimage mapping manager lessens the workload on physicians and researchers, permits more accurate data interpretation and analysis of scans, and allows physicians and researchers to more quickly reach a diagnosis of neuropsychiatric disease. In addition, the neuroimage mapping manager provides a decision support tool for clinicians in both clinical and research settings, to help them determine whether a therapy, such as talk therapy, pharmacotherapy, or mechanical electroconvulsive therapy, is effective as depicted via association of neuroimage data with the relevant medical literature. For instance, the neuroimage mapping manager may put a map of the portions of relevant medical literature onto a patient's scans for the diagnostic measurement of drug and/or treatment efficacy.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The invention can take the form of an entirely hardware embodiment, an entirely software embodiment or an embodiment containing both hardware and software elements. In a preferred embodiment, the invention is implemented in software, which includes but is not limited to firmware, resident software, microcode, etc.

Furthermore, the invention can take the form of a computer program product accessible from a computer-usable or computer-readable medium providing program code for use by or in connection with a computer or any instruction execution system. For the purposes of this description, a computer-usable or computer readable medium can be any tangible apparatus that can contain, store, or physically transport the program for use by or in connection with the instruction execution system, apparatus, or device.

The medium can be an electronic, magnetic, optical, electromagnetic, infrared, or semiconductor system (or apparatus or device). Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output or I/O devices (including but not limited to keyboards, displays, pointing devices, etc.) can be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

The description of the present invention has been presented for purposes of illustration and description, and is not intended to be exhaustive or limited to the invention in the form disclosed. Many modifications and variations will be apparent to those of ordinary skill in the art. The embodiment was chosen and described in order to best explain the principles of the invention, the practical application, and to enable others of ordinary skill in the art to understand the invention for various embodiments with various modifications as are suited to the particular use contemplated.

What is claimed is:

1. A computer implemented method for determining an efficacy of neuropsychiatric therapy, the computer implemented method comprising:
    a physical processor automatically comparing a first set of regions of interest in a first set of scans of a patient taken at a first time to a second set of regions of interest in a second set of scans of the patient generated at a second time period, by a neuroimage mapping manager, to create a comparison, wherein a region of interest is an area that shows an indication of a potential abnormality, an area that shows an indication of potential disease, or an area that is expected to change due to therapy;
    the physical processor identifying a set of changes in the regions of interest occurring over time based on the comparison;
    the physical processor searching a set of electronic medical literature sources for medical literature relevant to the set of changes in the regions of interest occurring over time to form relevant medical literature;
    the physical processor identifying portions of the relevant medical literature associated with the set of changes in the regions of interest; and
    the physical processor generating neuroimage mapping results, wherein the neuroimage mapping results comprises the set of changes in the regions of interest and a set of links to the portions of the relevant medical literature that are correlated to the regions of interest or the changes in the regions of interest.

2. The computer implemented method of claim 1 further comprising:
    the physical processor correlating clinical data for the patient to the set of changes in the regions of interest, wherein the results includes a set of links to portions of the clinical data for the patient corresponding to the changes in the regions of interest in the set of scans for the patient.

3. The computer implemented method of claim 1 further comprising:
    the physical processor, responsive to a determination that the set of changes in the regions of interest indicates a change in brain chemistry or brain metabolism, determining where the change in brain chemistry or brain metabolism occurs in the set of scans for the patient and identifying an amount of change in the brain chemistry or the brain metabolism, wherein the set of changes in the areas of interest comprises an identification of a location of the change in brain chemistry and brain metabolism and an indication of a degree of change in the brain chemistry and brain metabolism.

4. The computer implemented method of claim 1 further comprising:
the physical processor, responsive to a determination that the set of changes in the regions of interest indicates a change in brain chemistry or brain metabolism, determining whether the change in brain chemistry or brain metabolism correlates with clinical data for the patient; and
the physical processor identifying correlations between the changes in the brain chemistry and brain metabolism with the clinical data in the results.

5. The computer implemented method of claim 1 wherein the set of links to the portions of the relevant medical literature are embedded in the set of changes in the regions of interest.

6. The computer implemented method of claim 1 wherein the set of links to the portions of the relevant medical literature are stored in an electronic copy of a medical file for the patient.

7. The computer implemented method of claim 1 wherein the first set of scans and the second set of scans comprises at least one of a set of positron emission tomography scans of a brain of a patient and a set of magnetic resonance imaging scans of the brain of the patient.

8. The computer implemented method of claim 1 further comprising:
the physical processor, responsive to receiving the first set of scans for a patient generated at the first time, comparing the first set of scans to a set of baseline control scans to automatically identify the first set of regions of interest in the first set of scans, by the neuroimage mapping manager;
the physical processor, responsive to receiving the second set of scans for the patient generated at the second time, comparing the second set of scans to the set of baseline control scans to automatically identify the second set of regions of interest in the second set of scans, by the neuroimage mapping manager.

9. The computer implemented method of claim 8 wherein the set of baseline control scans comprises a set of baseline normal scans, and further comprising:
the physical processor receiving a set of brain scans for a set of healthy subjects in various demographic groups to form the baseline normal scans; and
the physical processor analyzing the baseline normal scans to identify a normal appearance of areas in normal brain scans, wherein a normal brain scan is a scan that does not show indications of disease or abnormalities in the areas in the normal brain scans.

10. The computer implemented method of claim 8 wherein the set of baseline control scans comprises a set of baseline abnormal scans, and further comprising:
the physical processor receiving a set of brain scans for a set of subjects in various demographic groups having identified abnormalities in the set of brain scans to form the baseline abnormal scans; and
the physical processor analyzing the baseline abnormal scans to identify an abnormal appearance of areas in brain scans, wherein an abnormal scan is a scan that shows indications of disease or abnormalities in the areas of the brain scans.

11. The computer implemented method of claim 8 wherein the set of baseline control scans comprises a set of baseline treatment scans, and further comprising:
the physical processor receiving a set of brain scans for a set of subjects in various demographic groups having identified conditions and undergoing identified therapies or treatments to form the baseline treatment scans; and
the physical processor analyzing the baseline treatment scans to identify an appearance of areas in brain scans during a course of at least one identified therapy or treatment, wherein a treatment scan is a scan that shows effects of treatments or therapies in the areas of the brain scans.

12. The computer implemented method of claim 1 wherein the neuroimage mapping results comprises the first set of regions of interest and the second set of regions of interest.

13. A computer program product for determining an efficacy of neuropsychiatric therapy, the computer program product comprising:
a computer usable medium having computer usable program code embodied therewith, said computer program product comprising:
computer usable program code configured to automatically compare a first set of regions of interest in a first set of scans of a patient taken at a first time to a second set of regions of interest in a second set of scans of the patient generated at a second time period, by a neuroimage mapping manager, to create a comparison, wherein a region of interest is an area that shows an indication of a potential abnormality, an area that shows an indication of potential disease, or an area that is expected to change due to therapy;
computer usable program code configured to identify a set of changes in the regions of interest occurring over time based on the comparison;
computer usable program code configured to search a set of electronic medical literature sources for medical literature relevant to the set of changes in the regions of interest occurring over time to form relevant medical literature;
computer usable program code configured to identify portions of the relevant medical literature associated with the set of changes in the regions of interest; and
computer usable program code configured to generate neuroimage mapping results, wherein the neuroimage mapping results comprises the set of changes in the regions of interest and a set of links to the portions of the relevant medical literature that are correlated to the regions of interest or the changes in the regions of interest.

14. The computer program product of claim 13 further comprising:
computer usable program code configured to correlate clinical data for the patient to the set of changes in the regions of interest, wherein the results comprise a set of links to portions of the clinical data for the patient corresponding to the changes in the regions of interest in the set of scans for the patient.

15. The computer program product of claim 13 further comprising:
computer usable program code configured to determine a location of a change in brain chemistry or a location of a change in brain metabolism in the first set of scans or the second set of scans and identifying an amount of change in brain chemistry or an amount of change in brain metabolism in response to a determination that the set of changes in the regions of interest indicates a change in brain chemistry or brain metabolism, wherein the set of changes in the areas of interest comprises an identification of the location of the change in brain chemistry and brain metabolism and an indication of a degree of change in brain chemistry and brain metabolism.

16. The computer program product of claim 13 further comprising:
   computer usable program code configured to determine whether a change in brain chemistry or a change in brain metabolism correlates with clinical data for the patient in response to a determination that the set of changes in the regions of interest indicates the change in brain chemistry or the change in brain metabolism; and
   computer usable program code configured to identify correlations between the changes in brain chemistry and brain metabolism with the clinical data in the results.

17. The computer program product of claim 13 further comprising:
   computer usable program code configured to, responsive to receiving the first set of scans for a patient generated at the first time, compare the first set of scans to a set of baseline control scans to automatically identify the first set of regions of interest in the first set of scans;
   computer usable program code configured to, responsive to receiving the second set of scans for the patient generated at the second time, compare the second set of scans to the set of baseline control scans to automatically identify the second set of regions of interest in the second set of scans.

18. The computer program product of claim 17 wherein the set of baseline control scans comprises a set of baseline normal scans, and further comprising:
   computer usable program code configured to receive a set of brain scans for a set of healthy subjects in various demographic groups to form the baseline normal scans; and
   computer usable program code configured to analyze the baseline normal scans to identify a normal appearance of areas in normal brain scans, wherein a normal brain scan is a scan that does not show indications of disease or abnormalities in the areas in the normal brain scans.

19. The computer program product of claim 17 wherein the set of baseline control scans comprises a set of baseline abnormal scans, and further comprising:
   computer usable program code configured to receive a set of brain scans for a set of subjects in various demographic groups having identified abnormalities in the set of brain scans to form the baseline abnormal scans; and
   computer usable program code configured to analyze the baseline abnormal scans to identify an abnormal appearance of areas in brain scans, wherein an abnormal scan is a scan that shows indications of disease or abnormalities in the areas of the brain scans.

20. The computer program product of claim 17 wherein the set of baseline control scans comprises a set of baseline treatment scans, and further comprising:
   computer usable program code configured to receive a set of brain scans for a set of subjects in various demographic groups having identified conditions and undergoing identified therapies or treatments to form the baseline treatment scans; and
   computer usable program code configured to analyze the baseline treatment scans to identify an appearance of areas in brain scans during a course of at least one identified therapy or treatment, wherein a treatment scan is a scan that shows effects of treatments or therapies in the areas of the brain scans.

21. An apparatus for managing neuropsychiatric disease data, the apparatus comprising:
   a neuroimage mapping manager for determining an efficacy of neuropsychiatric therapy, the neuroimage mapping manager comprising:
   a neuroimage analyzer, wherein the neuroimage analyzer automatically compares a first set of regions of interest in a first set of scans of a patient taken at a first time to a second set of regions of interest in a second set of scans of a patient generated at a second time period to create a comparison and identifies a set of changes in the regions of interest occurring over time based on the comparison wherein a region of interest is an area that shows an indication of a potential abnormality, an area that shows an indication of potential disease, or an area that is expected to change due to therapy; and
   a medical data and text analytics, wherein the medical data and text analytics searches a set of electronic medical literature sources for medical literature relevant to the set of changes in the regions of interest occurring over time to form relevant medical literature and identifies portions of the relevant medical literature associated with the set of changes in the regions of interest; and wherein the neuroimage mapping manager generates neuroimage mapping results, wherein the neuroimage mapping results comprises the set of changes in the regions of interest and a set of links to the portions of the relevant medical literature that are correlated to the regions of interest or the changes in the regions of interest.

22. The apparatus of claim 21 further comprising:
   a comparator, wherein the comparator correlates clinical data for the patient to the set of changes in the regions of interest, wherein the neuroimage mapping results comprises a set of links to portions of the clinical data for the patient corresponding to the changes in the regions of interest in the set of scans for the patient.

23. The apparatus of claim 21 further comprising:
   a set of computers, wherein the neuroimage mapping manager is located on the set of computers.

24. An apparatus comprising:
   a bus system;
   a communications system coupled to the bus system;
   a memory connected to the bus system, wherein the memory includes computer usable program code; and
   a processing unit coupled to the bus system, wherein the processing unit executes the computer usable program code to automatically compare a first set of regions of interest in a first set of scans of a patient taken at a first time to a second set of regions of interest in a second set of scans of the patient generated at a second time period, to create a comparison, wherein a region of interest is an area that shows an indication of a potential abnormality, an area that shows an indication of potential disease, or an area that is expected to change due to therapy; identify a set of changes in the regions of interest occurring over time based on the comparison of the first set of regions of interest to the second set of regions of interest; search a set of electronic medical literature sources for medical literature relevant to the set of changes in the regions of interest occurring over time to form relevant medical literature;
   identify portions of the relevant medical literature associated with the set of changes in the regions of interest; and generate neuroimage mapping results, wherein the neuroimage mapping results comprises the set of changes in the regions of interest and a set of links to the portions of the relevant medical literature that are correlated to the regions of interest or the changes in the regions of interest.

25. The apparatus of claim 24 wherein the processing unit further executes the computer usable program code to correlate clinical data for the patient to the set of changes in the regions of interest, wherein the results includes a set of links to portions of the clinical data for the patient corresponding to the changes in the regions of interest in the set of scans for the patient.

26. The apparatus of claim 24 wherein the first set of scans and the second set of scans comprises at least one of a set of positron emission tomography scans of a brain of a patient and a set of magnetic resonance imaging scans of the brain of the patient.

* * * * *